(12) United States Patent
Groszmann et al.

(10) Patent No.: US 8,526,688 B2
(45) Date of Patent: Sep. 3, 2013

(54) METHODS AND SYSTEMS FOR REGISTRATION OF SURGICAL NAVIGATION DATA AND IMAGE DATA

(75) Inventors: Daniel Eduardo Groszmann, Cambridge, MA (US); Vernon Thomas Jensen, Draper, UT (US); Gerald Lee Beauregard, Stratham, NH (US); Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 749 days.

(21) Appl. No.: 11/371,739

(22) Filed: Mar. 9, 2006

(65) Prior Publication Data

US 2007/0211927 A1 Sep. 13, 2007

(51) Int. Cl.
*G06K 9/00* (2006.01)
(52) U.S. Cl.
USPC ........... 382/128; 382/130; 382/131; 600/407; 600/410; 600/421; 600/423; 600/424; 600/426
(58) Field of Classification Search
USPC .................. 600/407, 424, 410, 423, 421, 426
See application file for complete search history.

(56) References Cited

U.S. PATENT DOCUMENTS

| | | | | |
|---|---|---|---|---|
| 5,563,988 | A * | 10/1996 | Maes et al. | 345/421 |
| 6,490,475 | B1 * | 12/2002 | Seeley et al. | 600/426 |
| 6,633,663 | B1 * | 10/2003 | Slesinger | 382/147 |
| 6,690,960 | B2 * | 2/2004 | Chen et al. | 600/407 |
| 6,834,201 | B2 * | 12/2004 | Gillies et al. | 600/411 |
| 7,123,008 | B1 * | 10/2006 | Damadian et al. | 324/309 |
| 7,356,918 | B2 * | 4/2008 | Okuda et al. | 29/833 |
| 7,375,521 | B1 * | 5/2008 | Damadian et al. | 324/307 |
| 7,499,806 | B2 * | 3/2009 | Kermani et al. | 702/19 |
| 7,664,303 | B2 * | 2/2010 | Zwirn et al. | 382/131 |
| 8,036,730 | B1 * | 10/2011 | Damadian et al. | 600/410 |
| 8,111,067 | B1 * | 2/2012 | Damadian et al. | 324/307 |
| 2003/0028094 | A1 * | 2/2003 | Kumar et al. | 600/410 |
| 2003/0135110 | A1 * | 7/2003 | Leussler | 600/422 |
| 2003/0158477 | A1 * | 8/2003 | Panescu | 600/424 |
| 2004/0152972 | A1 * | 8/2004 | Hunter | 600/424 |
| 2004/0171924 | A1 * | 9/2004 | Mire et al. | 600/407 |
| 2004/0199072 | A1 * | 10/2004 | Sprouse et al. | 600/424 |

(Continued)

*Primary Examiner* — Baisakhi Roy
(74) *Attorney, Agent, or Firm* — McAndrews, Held & Malloy, Ltd.; William Baxter

(57) ABSTRACT

Certain embodiments of the present invention provide a method for correlating data including: receiving from a tracking subsystem a first data set including a tracked position of an object; receiving from an imaging subsystem a second data set including an image of the object; and comparing automatically at least a portion of the first data set with at least a portion of the second data based at least in part on the tracked position of the object and the image of the object. In an embodiment, the comparing automatically the first data set with the second data set is performable in real-time. In an embodiment, the method further includes registering the first data set with the second data set. In an embodiment, the tracking subsystem tracks the object electromagnetically, at least in part. In an embodiment, the imaging subsystem includes an x-ray imaging subsystem. In an embodiment, the first data set is generatable by the tracking subsystem substantially in real-time. In an embodiment, the method further includes determining an offset between at least a portion of the first data set and at least a portion of the second data set. In an embodiment, the method further includes performing an adjustment based at least in part on the offset on at least one of: the tracking subsystem, the imaging subsystem, and a data processing subsystem.

21 Claims, 4 Drawing Sheets

(56) References Cited

U.S. PATENT DOCUMENTS

| | | | |
|---|---|---|---|
| 2004/0215071 A1* | 10/2004 | Frank et al. | 600/407 |
| 2006/0183993 A1* | 8/2006 | Horn | 600/407 |
| 2007/0106306 A1* | 5/2007 | Bodduluri et al. | 606/133 |
| 2008/0125647 A1* | 5/2008 | Rosengren et al. | 600/424 |
| 2008/0294258 A1* | 11/2008 | Revie et al. | 623/16.11 |

* cited by examiner

METHODS AND SYSTEMS FOR REGISTRATION OF SURGICAL NAVIGATION DATA AND IMAGE DATA

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present application relate generally to registering two or more data sets, generally for use in clinical applications. Particularly, certain embodiments relate to identifying differences between an output from an imaging subsystem with that of a tracking subsystem automatically.

Minimally invasive surgery ("MIS") may involve surgery performed by making relatively smaller entries into the body (as compared to those used in most traditional surgical procedures). Surgeons employing MIS may be able to perform procedures through incisions (or openings called ports) as small as 1/16 of an inch, for example. MIS may also be known as videoscopic surgery, "keyhole" surgery, laparoscopic surgery (laparoscopy), thoracoscopic surgery, or surgical endoscopy.

In order to improve effectiveness of MIS or other procedures such as interventional radiological procedures, it may be helpful to track the position of a surgical tool or an existing object in the patient using a navigation or tracking subsystem. An image of the patient may be generated prior to, and/or during the procedure, for example. Furthermore, clinicians practicing MIS or other procedures may prefer to employ a substantially real-time navigation or tracking system for tracking an objectin the patient prior to, or during the procedure. Consequently, it may be preferable to correlate, and/or register the output from the tracking subsystem with that of the imaging subsystem.

Sets of data acquired by sampling the same scene or object at different times, from different perspectives, or from different systems, may be in non-uniform coordinate systems. Registration may involve the process of transforming the different sets of data into one coordinate system. Registration may be preferable to compare or integrate the data obtained from different measurements, for example. In medical imaging, registration may additionally involve deformable registration to cope with deformable deformations of body parts imaged. Classic registration techniques such as point-pair and surface may not be practical for applications that involve substantially real-time navigation and/or tracking systems. Surgical remote tracking or navigation systems may determine a position and orientation of a navigated or existing object relative to a known reference, for example. A remote tracking or navigation system may be one in which an object for tracking is not physically integrated with the tracking or navigation device itself. During surgery, graphic overlays from the navigation or tracking subsystem may be used in conjunction with a radiological image to represent a surgical tool position and orientation with respect to the patient, for example. The image may be generated before surgery, or at some other time, for example.

One technique that may be used to visually compare the correspondence between the tracking or navigation system and the imaging subsystem may involve leaving a navigated tool in the image when a fluoroscopic image is acquired. System level accuracy may be gauged by observing the position of the tool graphic relative to the position of the actual tool in the image. The degree to which the tool graphic and actual tool image align, may be a good indicator of system accuracy.

However, such a visual test may only illustrate inaccuracies in one plane. To determine a correspondence in other planes may require repeating the test with additional images or tracking positions acquired from different angles. Further, the test may only provide visual feedback, and may not automatically quantify, or improve the misalignment or system accuracy, for example.

Misalignments of tool tracking and tool image may result from a bent or damaged tool or tool interface. Misalignment may also result from system calibrations, system variances, interferences (e.g. metal objects in a patient), and/or the like.

Thus, there is a need for methods and systems that register data from a tracking or navigation system with data from an imaging subsystem automatically. Additionally, there is a need for methods and systems that register data from a tracking or navigation system with data from an imaging subsystem in three or more dimensions. There is a need for methods and systems that register data from a tracking or navigation system with data from an imaging subsystem substantially in real-time. Further, there is a need for methods and systems that assist clinicians while performing procedures, such as MIS procedures.

BRIEF SUMMARY OF THE INVENTION

Certain embodiments of the present invention provide a method for correlating data including: receiving from a tracking subsystem a first data set including a tracked position of an object; receiving from an imaging subsystem a second data set including an image of the object; and comparing automatically at least a portion of the first data set with at least a portion of the second data based at least in part on the tracked position of the object and the image of the object. In an embodiment, the comparing automatically the first data set with the second data set is performable in real-time. In an embodiment, the method further includes registering the first data set with the second data set. In an embodiment, the tracking subsystem tracks the object electromagnetically, at least in part. In an embodiment, the imaging subsystem includes an x-ray imaging subsystem. In an embodiment, the second data set is generatable by the imaging subsystem substantially in real-time. In an embodiment, the method further includes determining an offset between at least a portion of the first data set and at least a portion of the second data set. In an embodiment, the method further includes performing an adjustment based at least in part on the offset on at least one of: the tracking subsystem, the imaging subsystem, and a data processing subsystem. In an embodiment, the offset includes information in at least three dimensions. In an embodiment, the registering the first data set with the second data set is performable in at least three dimensions. In an embodiment, the second data set includes an image of at least a portion of the tracking subsystem, and wherein registration of the first data set with the second data set is based at least in part on the image of at least a portion of the tracking subsystem Certain embodiments of the present invention provide a system for registering data including: a tracking subsystem for tracking a position of an object, the tracking subsystem capable of providing a first data set including the position of the object; an imaging subsystem for generating an image of an object, the imaging subsystem capable of providing a second data set including the image of the object; and a data processing subsystem capable of communications with the tracking subsystem and the imaging subsystem, wherein the data processing subsystem is capable of receiving the first data set and the second data set, wherein the data processing subsystem is capable of automatically comparing the first data set with the second data set. In an embodiment, the data processing subsystem is capable of registering the first data set with the second data set. In an embodiment, the data processing subsystem is capable of adjusting in response to the automatically comparing the first data set with the second data set at least one of: the tracking subsystem, the imaging subsystem, and a data processing subsystem. In an embodiment, the tracking subsystem includes an electromagnetic navigation subsystem. In an embodiment, the imaging subsystem includes a fluoroscopic imaging subsystem. In an embodiment, the object includes an antenna pattern, the pattern substantially opaque to x-rays. In an embodiment, the system is capable of functioning substantially in real-time. In an embodiment, the first data set and the second data set include at least three dimensional information.

Certain embodiments of the present invention provide a computer-readable storage medium including a set of instructions for a computer, the set of instructions including: a reception routine for receiving from a tracking subsystem a first data set including a tracked position of an object; a reception routine for receiving from an imaging subsystem a second data set including an image of the object; and a comparison routine for comparing automatically at least a portion of the first data set with at least a portion of the second data based at least in part on the tracked position of the object and the image of the object. In an embodiment, the set of instructions further includes a registration routine for registering the first data set with the second data set. In an embodiment, the set of instructions further includes an adjustment routine for performing an adjustment based at least in part on the automatic comparison of the first data set and the second data set on at least one of: the tracking subsystem, the imaging subsystem, and a data processing subsystem.

Figure 1:
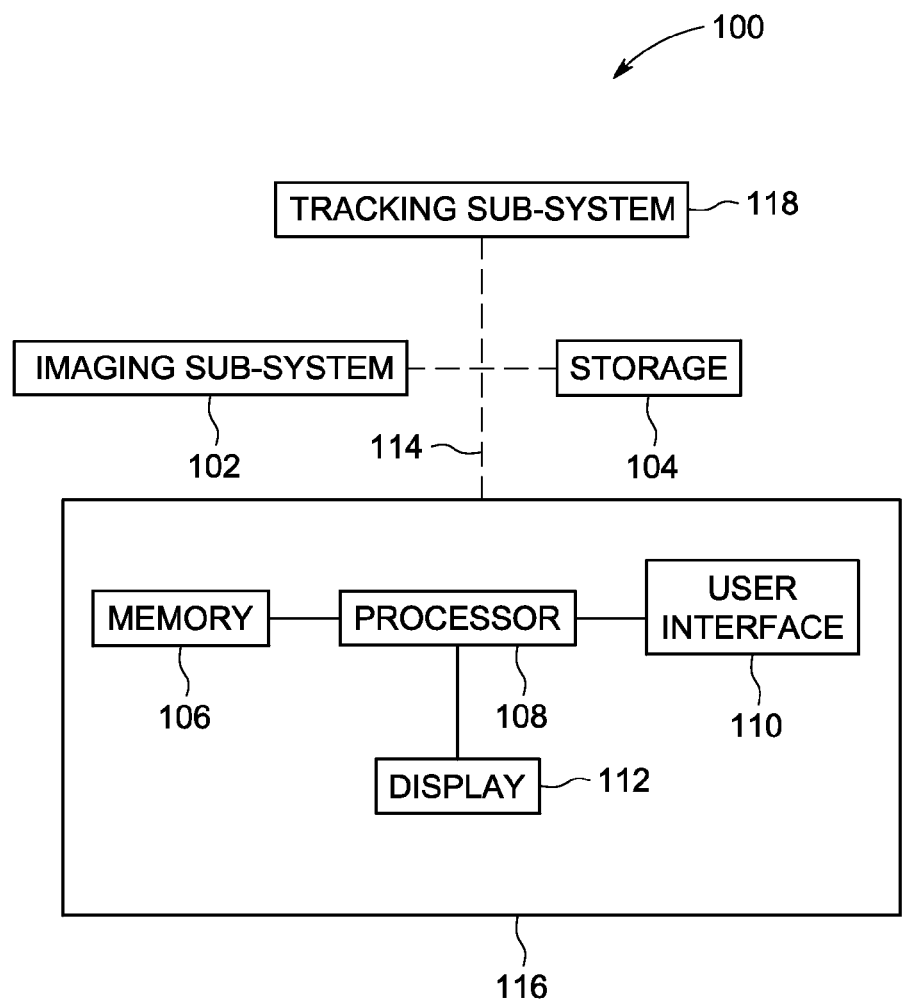
FIG. 1 shows a system for registering image data, and tracking and/or navigation data, in accordance with an embodiment of the present invention.

The foregoing summary, as well as the following detailed description of certain embodiments of the present application, will be better understood when read in conjunction with the appended drawings. For the purpose of illustrating the invention, certain embodiments are shown in the drawings. It should be understood, however, that the present invention is not limited to the arrangements and instrumentality shown in the attached drawings. Further, some figures may be representations of the type of display and/or output associated with methods and systems of the present invention, in accordance with one or more embodiments.

DETAILED DESCRIPTION OF THE INVENTION

FIG. 1 shows a system 100 for registering image data, and tracking and/or navigation data, in accordance with an embodiment of the present invention. A system 100 may include an imaging subsystem 102 communicatively linked to a data processing subsystem 116, tracking subsystem 118, and/or a storage 104 through one or more communications links 114.

An imaging subsystem 102 may be any radiological system capable of generating two-dimensional, three-dimensional, and/or four-dimensional data corresponding to a volume of interest of a patient, potentially including foreign objects therein. Some types of image processing subsystems 102 include computed tomography (CT), magnetic resonance imaging (MRI), x-ray, positron emission tomography (PET), tomosynthesis, ultrasound, and/or the like, for example. An imaging subsystem 102 may include a fluoroscopic and/or angiographic system, for example. An imaging subsystem 102 may be capable of generating images of at least a portion of a volume of interest substantially in real-time, for example. An imaging subsystem 102 may generate one or more data sets including image data which may be communicated over a communications link 114 to a storage 104 and/or a data processing subsystem 116.

A tracking subsystem 118 may be any system capable of tracking a position of an object, for example. An object is a potentially remote object. By potentially remote object, it may be understood that the object is capable of being tracked without being integrated physically with the tracking subsystem 118 itself. An object may include an object previously existing in a patient, such as a bone screw, for example. An object may also include a surgical tool, a navigational tool, a guidewire, a catheter, and/or the like, for example. An object may be incorporated or form a portion of a surgical tool, a navigational tool, and/or an existing object such as a bone screw, for example. An object and/or a tracking subsystem 118 may include one or more fiducials, such as anything capable of providing a reference for one or more systems, such as tracking subsystem 118 and/or imaging subsystem 102, for example. A fiducial may be, for example a BB, or an antenna pattern, for example. An object may include, for example, a microsensor capable of being tracked by an antenna, such as an electromagnetic antenna array, for example. An object may be passive (e.g. no power source), or active (e.g. power source supplying power to object), for example. For example, an object may transmit electromagnetic energy, such as radio, microwave, and/or light. Such energy may include a signal comprising information which may be converted into position information on one or more dimension, for example. An object may include an antenna, having an antenna design, such as a distinctive coil, a pattern, and/or the like, for example.

The tracking subsystem 118 may include one or more transmitters and/or receivers, for example. A transmitter and/or receiver may be integrated into the object, for example. A receiver and/or transmitter may include an antenna, such as an electromagnetic antenna array, for example. An antenna may be positioned proximally to a volume of interest and may track a position of an object. A tracking subsystem 118 may also include a reference point from which a position of an object is referenced to. Such a reference may be an antenna, such as a proximally placed antenna array, for example.

A tracking subsystem 118 may be capable of tracking a position of an object in one, two, three, and/or four dimensions (e.g. three dimensions over time), for example. A tracking subsystem 118 may provide as an output one or more signals including a data set, for example. The data set may include information regarding the position of the object with respect to a reference (e.g. an antenna array), for example. The data set may include information regarding the position of an object in one, two, three, and/or four dimensions, for example. The output may be provided to a storage 104 and/or data processing subsystem 116, for example, either automatically or on-demand, for example. The tracking subsystem 118 may track a position of one or more objects automatically, or through user intervention, for example. The tracking subsystem 118 may track a position of one or more objects substantially in real-time, for example. The tracking subsystem 118 may be designed for interventional and/or surgical applications, such as MIS, for example. The tracking subsystem 118 may track the position of an object by transmitting and/or receiving electromagnetic energy, such as 14.7 kHz radio waves, for example. Further, the tracking subsystem 118 may employ optical tracking technologies, such as light emitting diodes and/or optically reflective spheres, for example. The tracking subsystem 118 may be one or more separate components, or may be integrated with other of the components in system 100, such as data processing subsystem 116, storage 104, and/or imaging subsystem 102, for example.

Figure 4:
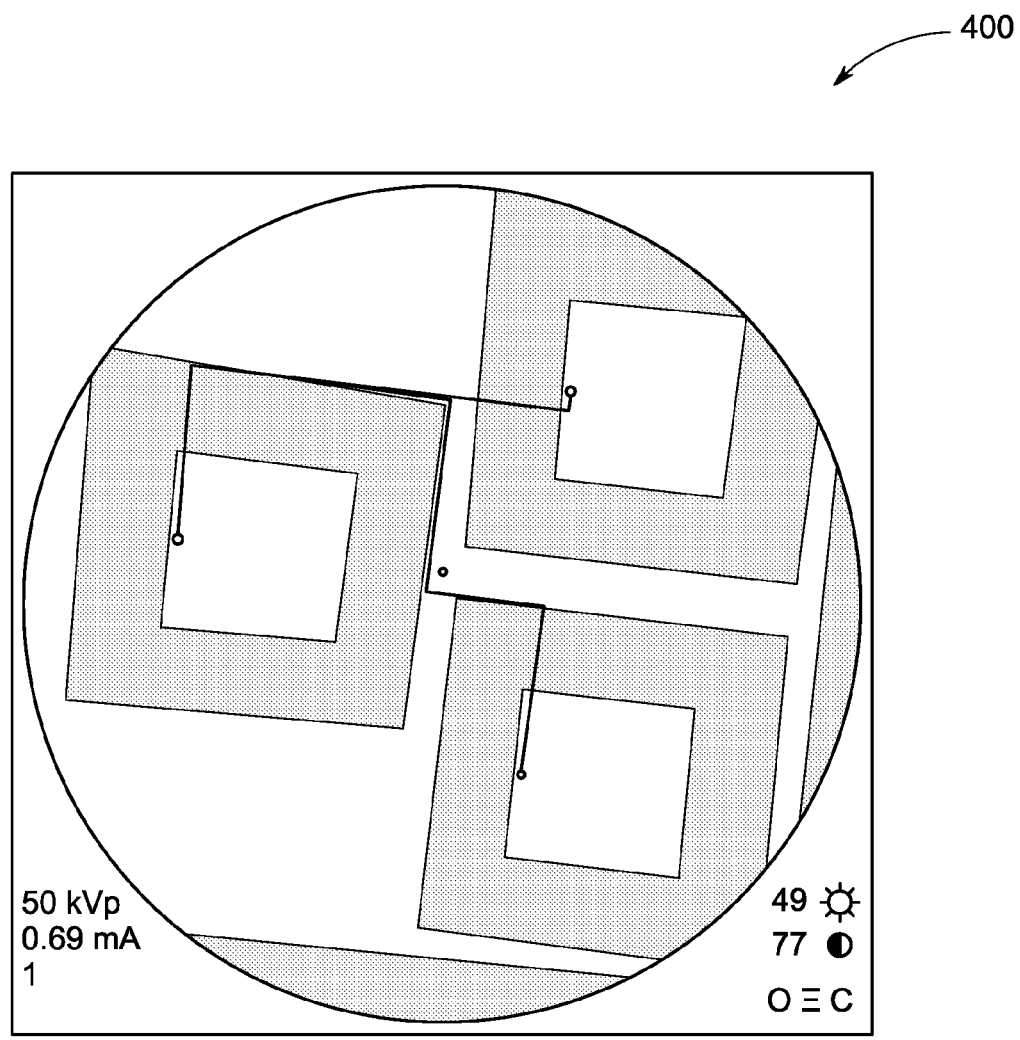
FIG. 4 shows a radiological image of an electromagnetic antenna array 400, in accordance with an embodiment of the present invention.

Turning for a moment to FIG. 4, a radiological image of an electromagnetic antenna array 400 is shown, in accordance with an embodiment of the present invention. An electromagnetic antenna array, similar to the one 400 shown in FIG. 4, may be included in tracking subsystem 118, for example. It may further be possible to image the antenna array, as shown in FIG. 4, for example, in one, two, three, and/or four dimensions, for example. Antenna array 400 is shown in FIG. 4 in two dimensions. The center dot may indicate a center reference point of the antenna array. Such a reference point may be similar to that used for tracking the object, for example. The additional dots shown in array 400 may further define the reference and/or coordinates of the antenna array, for example. The dots may be automatically detectable, for example, by a data processing subsystem, such as subsystem 116, for example. Further, the pattern of the array may be automatically detectable by a data processing subsystem to determine a reference and/or coordinates for the tracking subsystem 118, for example.

Turning back to FIG. 1, a storage 104 may be capable of storing set(s) of data generated by the imaging subsystem 102 and/or tracking subsystem 118, for example. The storage 104 may be, for example, a digital storage, such as a PACS storage, an optical medium storage, a magnetic medium storage, a solid-state storage, a long-term storage, a short-term storage, and/or the like. A storage 104 may be integrated with imaging subsystem 102, tracking subsystem 118, and/or data processing subsystem 116, for example. A storage 104 may be locally or remotely located, for example. A storage 104 may be persistent or transient, for example.

A data processing subsystem 116 may further include a memory 106, a processor 108, a user interface, 110 and/or a display 112. The various components of a data processing subsystem 116 may be communicatively linked. Some of the components may be integrated, such as, for example processor 108 and memory 106. A data processing subsystem 116 may receive data corresponding to a volume of interest of a patient from either an imaging subsystem 102, storage 104, and/or tracking subsystem 118, for example. The data processing subsystem 116 may be communicatively linked to the imaging subsystem 102, storage 104, and/or tracking subsystem 118 through one or more networks 114, for example. Communications between various components of system 100 may be continuous, intermittent, on-demand, and/or the like, for example. Data received by data processing subsystem 116 may be stored in memory 106, for example.

A memory 106 may be a computer-readable memory, for example, such as a hard disk, floppy disk, CD, CD-ROM, DVD, compact storage, flash memory, random access memory, read-only memory, electrically erasable and programmable read-only memory and/or other memory. A memory 106 may include more than one memories for example. A memory 106 may be able to store data temporarily or permanently, for example. A memory 106 may be capable or storing a set of instructions readable by processor 108, for example. A memory 106 may also be capable of storing data generated by image generation subsystem 102, for example. A memory 106 may also be capable of storing data generated by processor 108, for example.

A processor 108 may be a central processing unit, a microprocessor, a microcontroller, and/or the like. A processor 108 may include more than one processors, for example. A processor 108 may be an integrated component, or may be distributed across various positions, for example. A processor 108 may be capable of executing an application, for example. A processor 108 may be capable of executing any of the methods in accordance with the present invention, for example. A processor 108 may be capable of receiving input information from a user interface 110, and generating output displayable by a display 112, for example.

A user interface 110 may include any device(s) capable of communicating information from a user to a data processing subsystem 116, for example. A user interface 110 may include a mousing device (e.g. a mouse), keyboard, and/or any other device capable of receiving a user directive. For example a user interface 110 may include voice recognition, motion tracking, and/or eye tracking features, for example. A user interface 110 may be integrated into other components, such as display 112, for example. As an example, a user interface 110 may include a touch responsive display 112, for example.

A display 112 may be any device capable of communicating visual information to a user. For example, a display 112 may include a cathode ray tube, a liquid crystal diode display, a light emitting diode display, a projector and/or the like. A display 112 may be capable of displaying radiological images and data generated by data processing subsystem 116, for example. A display may be two-dimensional, but may be capable of indicating three-dimensional information through shading, coloring, and/or the like.

Figure 2:
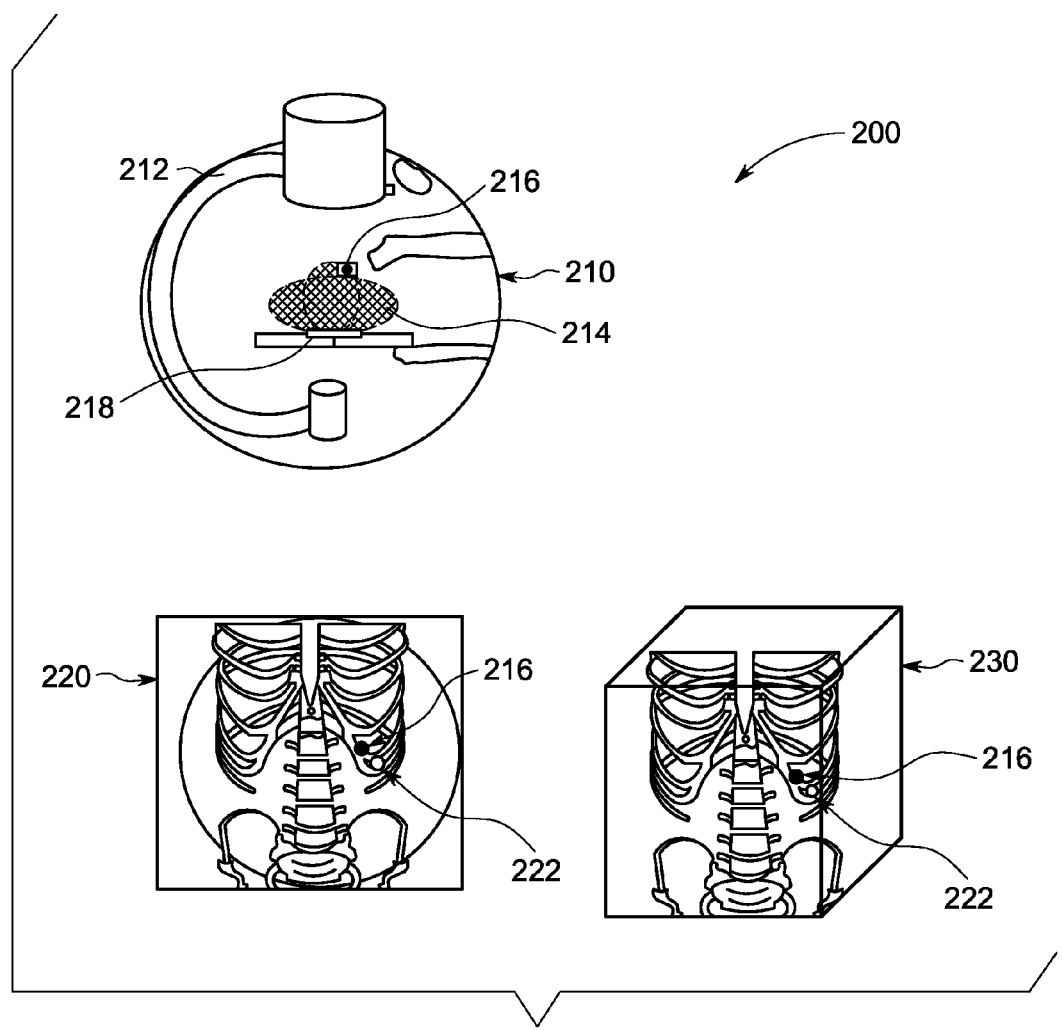
FIG. 2 shows a representation of a tracking subsystem and an imaging subsystem with respect to a volume of interest, in accordance with an embodiment of the present invention.

FIG. 2 shows a series 200 of representations 210, 220, and 230 pertaining to a tracking subsystem and an imaging subsystem with respect to a volume of interest, in accordance with an embodiment of the present invention. Representation 210 shows a tracking subsystem 218 (e.g. similar to tracking subsystem 118) and an imaging subsystem 212 (e.g. similar to imaging subsystem 102) with respect to a volume of interest 214 and an object 216. The tracking subsystem may include an electromagnetic antenna array, such as that shown in FIG. 4, for example. Representation 220 shows a two dimensional image from the volume of interest 214. Representation 220 further shows the tracked position 222 of the object 216 (from the tracking subsystem 218), and the imaged position 224 of object 216 (from the imaging subsystem 212). Representation 230 is similar to representation 220. However, representation 230 shows the volume of interest imaged in three dimensions, and correspondingly, the tracked position 222 and imaged position 224 of the object 216 are shown in three dimensions as well.

Thus, representations 220 and 230 show integrated data—image data from the imaging subsystem 212 and tracking data from the tracking subsystem 218. As can be seen from representations 220 and 230, the tracked position 222 and the imaged position 224 are not identical. The difference between the tracked position 222 and imaged position 224 may yield offset data, for example. Offset data may be employed for accurately registering image data with tracking data, for example. Offset data may also be helpful for calibrating a tracking subsystem 218, an imaging subsystem 212, and/or a data processing subsystem (e.g. subsystem 116), for example. Offset data may also be used to alert physicians with regards to the offset, for example. For example, offset data may be of the type indicative of a damaged surgical tool.

Tracking data may represent the position of a sensor and/or object in space over time as well as the orientation, or pose, of a sensor and/or object in the same space, for example. Orientation data may be used to determine where the sensor and/or object is pointing in space, for example.

Figure 3:
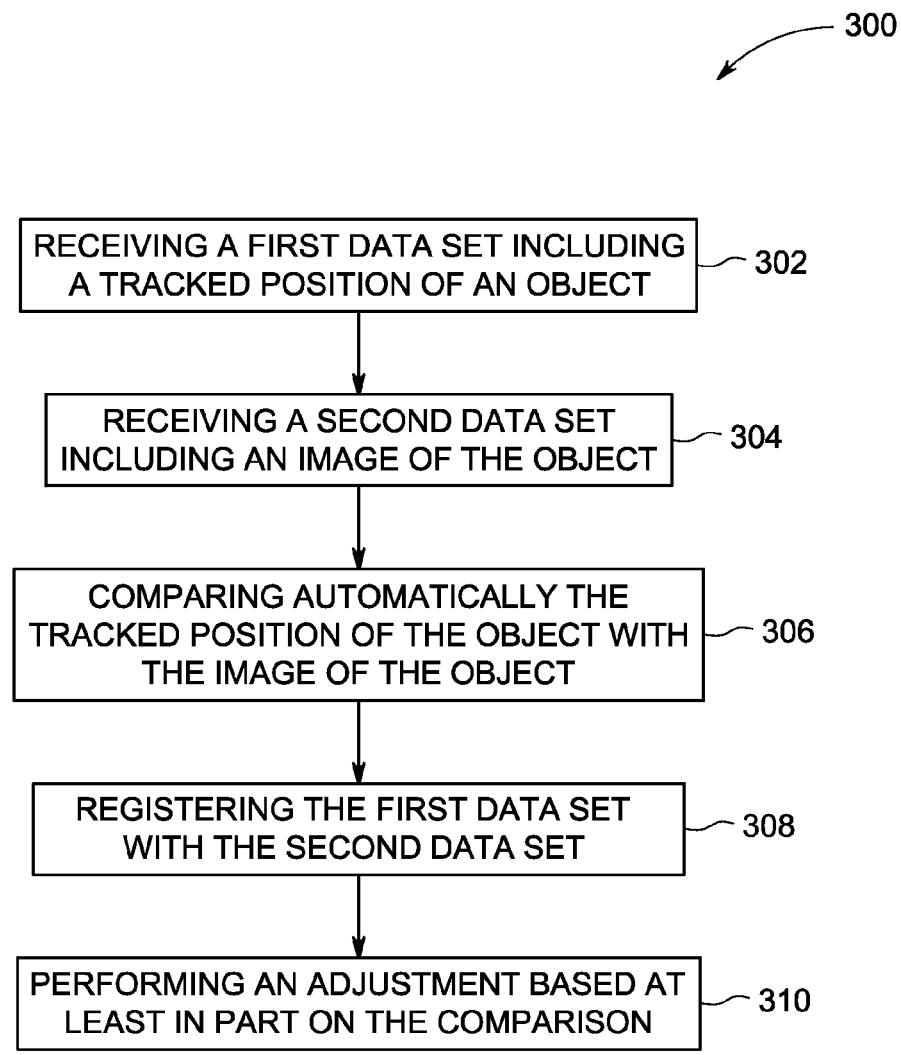
FIG. 3 shows a method for correlating data, in accordance with an embodiment of the present invention.

FIG. 3 shows a method 300 for correlating data, in accordance with an embodiment of the present invention. The steps of method 300 may be performed in an alternate order as shown, for example. At least some of the steps of method 300 may be performed simultaneously or substantially simultaneously, for example. Furthermore, some steps of method 300 (or portions thereof) may be omitted (e.g. steps 308 and/or 310), for example. The steps of method 300 may be performed by a computer and/or other processor (such as data processing subsystem 116 and/shown in FIG. 1) executing a set of instructions on a computer-readable medium, for example.

At step 302 a first data set including a tracked position (e.g. position 222 shown in FIG. 2) of an object (e.g. object 216 shown in FIG. 2) is received from a tracking subsystem (e.g. subsystem 118 shown in FIG. 1). A first data set may be received by a data processing subsystem (e.g. subsystem 116 shown in FIG. 1), for example. The tracked position of the object may be in one, two, three, and/or four dimensions, for example. The tracked position of the object may be with respect to a particular reference, for example. Such a reference may be incorporated into a tracking subsystem, for example. Such a reference may be an electromagnetic antenna array, such as that shown in FIG. 4, for example, or a portion thereof, for example. The first data set may be received substantially in real-time, for example. A surgeon may move an instrument, and the first data set may substantially track the position of the instrument in real-time, for example. The first data set may include more than one tracked positions corresponding to a plurality of objects, for example. Such objects may include those discussed in conjunction with tracking subsystem 118 (shown in FIG. 1). The first data set may be automatically received, or may be received in response to a user interaction, for example. The first data set may include historical (e.g. not real-time) information regarding an object in a volume of interest (e.g. an implant), for example. Such historical information may be storable in a storage (e.g. storage 104), for example. Position information may include coordinate positioning data and/or orientation information, for example. Orientation may be further obtained by tracking positions of more than one object, for example.

At step 304 a second data set including an image of the object (e.g. image 224 shown in FIG. 2) is received from an imaging subsystem (e.g. subsystem 102 shown in FIG. 1). The second data set may be received by a data processing subsystem (e.g. subsystem 116 shown in FIG. 1), for example. The image of the object may be in one, two, three, and/or four dimensions, for example. Imaging of the object may be facilitated by configuring the object to include an x-ray opaque feature (e.g. a fiducial), for example. Such a feature may be a simple pattern (e.g. circular/spherical) or more complex (e.g. a pattern and/or an array), for example. The feature may be selected based on the ability to automatically recognize such a feature (e.g. with a data processing subsystem 116 or imaging subsystem 102), for example. A plurality of feature-types may correspond to a plurality of objects, for example. One feature-type may correspond to one type of surgical instrument, and another feature-type may correspond to a different type of surgical instrument (or, for example, an implant), for example. In such a way, it may be possible to automatically detect which object has which location, for example. This concept may be further adapted to provide orientation image information for an object, for example. For example, an object may have a particular image appearance from one angle, and a different image appearance from a second angle. If such features are automatically detectable, it may be possible to automatically determine an orientation of the object, for example. Any such feature may be selected so as not to substantially compromise the clinical value of a corresponding image, for example.

The image of the object may be with respect to a particular reference, for example. Such a reference may be incorporated into an imaging subsystem, for example. Such a reference may be a fiducial, such as a marker on an x-ray detector, for example. Like the object, it may be possible to design such a fiducial to be automatically detectable by a data processing subsystem (e.g. subsystem 116). The second data set may be received substantially in real-time, for example. The second data set may be received during an interval of time relatively soon before a procedure, for example. One or more second data set(s) may be periodically received before, during, and after a procedure, for example. Additional second data set(s) may be received periodically, for example, for recomparison and/or reregistration, for example. A surgeon may move an instrument, and the second data set may substantially show the image of the instrument with respect to a reference and/or a volume of interest in real-time, for example. A second data set may show an object at a specific point in time, for example. The second data set may include more than one image(s) corresponding to a plurality of objects, for example. Such objects may include those discussed in conjunction with tracking subsystem 118 (shown in FIG. 1). The second data set may be automatically received, or may be received in response to a user interaction, for example. The second data set may include historical (e.g. not real-time) information regarding an object in a volume of interest (e.g. an implant). Such historical information may be storable in a storage (e.g. storage 104).

At step 306, at least a portion of the first data set is automatically compared with at least a portion of the second data set based at least in part on the tracked position of the object and the image of the object. The first data set may be compared with the second data set by a data processing subsystem (e.g. subsystem 116 shown in FIG. 1), for example. A slice of the first data set may be compared with a corresponding slice of the second data set, for example. An angle view of the first data set may be compared with a corresponding angle view of the second data set, for example. A reconstructed volume first data set (or a portion thereof) may be compared with a corresponding reconstructed volume second data set (or a corresponding portion thereof), for example. Automatic comparison may be facilitated by automatic recognition of the image of the object, for example. For example, image processing algorithms may detect automatically the object. For example, image processing algorithms may be facilitated by the opacity, shape, and/or other aspects of the object as discussed above. Step 306 may be performable in one, two, three, and/or four dimensions, for example. Step 306 may be performable substantially in real-time, for example. Step 306 may also involve a user intervention and/or interaction, if preferable, for example. Automatic comparison may be helpful for determining the tracking subsystem accuracy, for example. Automatic comparison may be helpful for determining the imaging subsystem accuracy, for example. Automatic comparison may be helpful for determining the data processing subsystem accuracy, for example. Automatic comparison may be helpful for determining if an object, such as a surgical tool, may be damaged and/or malformed, for example. Automatic comparison may result in offset data, for example. Such offset data may include information in one, two, three, and/or four dimensions, for example.

At step 308, the first data set is registered with the second data set. The first data set may be registered with the second data set by a data processing subsystem (e.g. subsystem 116 shown in FIG. 1), for example. Registration may involve the correlation between the first data set and the second data set, for example. For example, a uniform coordinate system may be determined based on the data sets. Registration of data sets may be helpful for aligning the tracked tool position with the image on a display and/or otherwise, for example. Registration may result in a single, integrated data set, for example. Registration may result in a scaling or adjustment to one or both of the first and/or second data sets, for example. Registration may result in a third "registered" data set, for example, having a registered coordinate system, for example. Step 308 may be performable in one, two, three, and/or four dimensions, for example. Step 308 may be performable substantially in real-time, for example. Step 308 may also be performable automatically and/or with a user intervention and/or interaction, if preferable, for example. The registration process may result in offset data, for example.

At step 310 an adjustment is performed based at least in part on the comparison and/or registration. Adjustment may be based at least in part on offset data, such as offset data generated in steps 306 and/or 308, for example. The adjustment may be performed on some and/or all of the subsystems and/or components discussed above, for example. For example, adjustment may be performed on the tracking subsystem, the imaging subsystem, and/or the data processing subsystem, and/or a portion thereof. Step 310 may be performable in one, two, three, and/or four dimensions, for example. Step 310 may be performable substantially in real-time, for example. Step 310 may be performable automatically and/or may involve a user intervention and/or interaction, if preferable, for example. An adjustment may include warning and/or alerting a user and/or a machine of potential inaccuracies, for example. An adjustment may involve re-registering data sets (e.g. repeating step 308) and/or re-comparing data sets (e.g. repeating step 306), for example. An adjustment may serve to correct inaccuracies, for example. Collecting misalignment information from multiple angles may provide enough information to perform adjustments in three and/or more dimensions, for example. For example three-dimensional fluoroscopy data including multiple views of the object may provide sufficient information for three or more dimensions of adjustment.

In three-dimensional fluoro applications and/or other three-dimensional and/or four-dimensional radiological imaging modalities, volumetric datasets may be created by back-projecting multiple two-dimensional fluoroscopic images, for example. Such applications may facilitate method 300, for example, with steps 306, 308, and/or 310 by providing enough information to calculate precise position and orientation offsets between image object position and the tracked object position. When offsets are known, it may also be possible to use them to report system accuracy, or even to use them for on-the fly re-registration (e.g. repeat step 308), for example. This can be used to close the loop (e.g. automatically and/or with user interaction) between the tracked object position and imaged object position information, for example.

As an illustrative example of method 300, a data processing subsystem is configured to automatically compare a first and a second data set. The first data set is received substantially in real-time during the procedure from a three-dimensional electromagnetic (EM) surgical tracking subsystem. The second data set is received at the outset of the procedure from a three-dimensional fluoroscopic imaging subsystem.

The object is incorporated into the tip of the surgical tool. The object is substantially passive (e.g. no active power source), and has a readily identifiable antenna design. The antenna design varies from various viewing angles. Portions of the antenna are substantially opaque for x-rays such that, for example the imaging subsystem may determine the position and/or orientation of the antenna.

The surgical tracking subsystem tracks the position and orientation of the object with an antenna located below the patient's volume of interest. The antenna below the patient also serves as a reference for the tracked position of the object. The tracking subsystem tracks the object substantially in real-time, and provides an output (e.g., the first data set) containing this information substantially in real-time. Similarly, the imaging subsystem images the position and the orientation of the object with fluoroscopic imaging techniques. The imaging subsystem images the object at the beginning of the procedure, and periodically during the procedure for re-comparison and/or re-registration, and provides a corresponding output (e.g. the second data set) substantially in real-time.

The data processing subsystem receives the first and second data sets. The data processing subsystem then automatically identifies the position and orientation of the object in the second data set. Automatic identification of the object is facilitated by the data processing subsystem knowing in advance what the antenna patterns are for the particular object. The image also contains at least a portion of the tracking antenna below the patient's volume of interest. Again, the data processing subsystem automatically detects the tracking antenna based on the particular antenna pattern of the tracking antenna.

The data processing subsystem then compares automatically the position of the object in the first set of data (EM tracking subsystem data in three dimensions) with the position of the object in the second set of data (fluoroscopic data in three dimensions). In both sets of data, the object is automatically referenced to the tracking antenna. The data processing subsystem compares the two sets of data, and detects a difference between the object positions. The data processing subsystem also detects no difference between the object orientations. Consequently, the data processing subsystem determines that the data from the tracking subsystem should be adapted to conform with that of the imaging subsystem. Thus, the data processing subsystem registers the data by adapting and scaling the tracking subsystem data accordingly. It may have also been possible to scale imaging subsystem data and/or both tracking and imaging data to accomplish registration. The tracking subsystem data and imaging subsystem data are integrated and outputted to a display substantially in real-time. Thus, the clinician views the integrated tracking subsystem and imaging subsystem data in a single view.

Once the data sets are registered, it is not necessary to perform substantially real-time imaging through the fluoroscopy system. Consequently, only the tracking subsystem data is substantially real-time. The fluoroscopy system may be automatically reactivated at subsequent times to ensure that the tracking and imaging data are properly registered, and/or whether subsequent system adjustments should be made, for example.

Thus, embodiments of the present application provide methods and systems that register data from a tracking or navigation system with data from an imaging subsystem automatically. Additionally, embodiments of the present application provide methods and systems that register data from a tracking or navigation system with data from an imaging subsystem in three or more dimensions. Embodiments of the present application provide methods and systems that register data from a tracking or navigation system with data from an imaging subsystem substantially in real-time. Further, embodiments of the present application provide methods and systems that assist clinicians while performing procedures, such as MIS and/or interventional procedures.

In an embodiment, a data processing subsystem (e.g. subsystem 116) includes a computer-readable medium, such as a hard disk, floppy disk, CD, CD-ROM, DVD, compact storage, flash memory and/or other memory. The medium may be in memory (e.g. memory 106), processor (e.g. processor 108) and/or in a separate system. The medium may include a set of instructions capable of execution by a computer or other processor. The receiving, comparing, registering, and/or adjusting functions described above may be implemented as instructions on the computer-readable medium. For example, the set of instructions may include a reception routine for receiving a first set of data. Additionally, the set of instructions may include a reception routine for receiving a second set of data. In an embodiment, the set of instructions may include an automatic comparison routine for automatically comparing at least a portion of the first and second data sets. In an embodiment, the set of instructions may further include a registration routine for registering the first and second sets of data. In an embodiment the set of instructions may further include an adjustment routine for adjusting at least one of a variety of system aspects in response to a comparison of the data sets.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

The invention claimed is:

1. A method for correlating radiological data comprising:
   receiving from a radiological tracking subsystem a first data set including a tracked position of an object, wherein the object comprises an antenna pattern;
   receiving from a radiological imaging subsystem a second data set including an image of the antenna pattern of the object;
   automatically recognizing, by a data processing subsystem, the antenna pattern in the second data set to determine an imaged position of the object in the second data set; and
   comparing automatically, by the data processing subsystem, at least a portion of the first data set with at least a portion of the second data based at least in part on the tracked position and the imaged position of the object.

2. The method of claim 1, wherein the comparing automatically the first data set with the second data set is performable in real-time.

3. The method of claim 1 further comprising registering the first data set with the second data set.

4. The method of claim 3, wherein the registering the first data set with the second data set is performable in at least three dimensions.

5. The method of claim 1, wherein the radiological tracking subsystem tracks the object electromagnetically, at least in part.

6. The method of claim 1, wherein the radiological imaging subsystem includes an x-ray imaging subsystem.

7. The method of claim 1, wherein the first data set is generatable by the tracking subsystem substantially in real-time.

8. The method of claim 1 further comprising determining an offset between at least a portion of the first data set and at least a portion of the second data set.

9. The method of claim 8 further comprising performing an adjustment based at least in part on the offset on at least one of the radiological tracking subsystem, the radiological imaging subsystem, or a data processing subsystem.

10. The method of claim 8, wherein the offset comprises information in at least three dimensions.

11. The method of claim 1, wherein the second data set comprises an image of at least a portion of the radiological tracking subsystem, and wherein registration of the first data set with the second data set is based at least in part on the image of at least a portion of the radiological tracking subsystem.

12. The method of claim 1, wherein the antenna pattern comprises an antenna array and center dot arranged to indicate a center reference point of the antenna array.

13. The method of claim 12, wherein the antenna pattern comprises at least one additional dot arranged to define at least one of a reference of the antenna array or a coordinate of the antenna array.

14. The method of claim 1, wherein the antenna pattern comprises at least one additional dot arranged to define at least one of a reference of the antenna array or a coordinate of the antenna array.

15. The method of claim 1, wherein the antenna pattern comprises a first appearance when viewed from a first angle and a second appearance when viewed from a second angle.

16. The method of claim 15 further comprising automatically determining, by the data processing subsystem, an orientation of the object according to at least one of the first appearance or the second appearance.

17. The method of claim 15 further comprising:
   collecting misalignment information according to each of the first appearance of the antenna pattern and the second appearance of the antenna pattern; and
   registering the first data set with the second data set in three dimensions according to the misalignment information.

18. The method of claim 1, wherein a feature of the antenna pattern corresponds to a type of the object.

19. The method of claim 18 further comprising:
   automatically recognizing, by the data processing subsystem, the feature of the antenna pattern; and
   automatically identifying, by the data processing subsystem, the type of the object according to the feature of the antenna pattern.

20. The method of claim 18, wherein the object comprises at least one of an implant, a catheter, a guidewire, a first surgical instrument, or a second surgical instrument.

21. The method of claim 1, wherein the antenna pattern comprises at least one of a distinctive:
- coil,
- shape, and
- opacity.

* * * * *